United States Patent [19]

Schlein

[11] Patent Number: 4,516,572
[45] Date of Patent: May 14, 1985

[54] PERFORATED CLOSED CELL PADDING MATERIAL

[76] Inventor: Allen P. Schlein, 107 Curtis Ter., Fairfield, Conn. 06430

[21] Appl. No.: 474,287

[22] Filed: Mar. 11, 1983

[51] Int. Cl.$^3$ ............................................ A61L 15/00
[52] U.S. Cl. .................................................. 128/156
[58] Field of Search ................ 128/90, 155, 156, 89, 128/82; 428/159, 314.4, 314.8

[56] References Cited

U.S. PATENT DOCUMENTS

| 3,881,473 | 5/1975 | Corvi et al. | 128/90 |
| 3,882,857 | 5/1975 | Woodall, Jr. | 128/90 |
| 3,938,509 | 2/1976 | Barber | 128/89 R X |
| 4,294,240 | 10/1981 | Thill | 128/156 |

Primary Examiner—John D. Yasko
Attorney, Agent, or Firm—Spencer E. Olson

[57] ABSTRACT

Perforated closed cell polyvinyl chloride foam padding material useful with an immobilizing orthopedic cast, said material being capable of transporting moisture along the surface thereof in contact with the human skin and of passing moisture such as water and perspiration from the human skin therethrough by vapor transmission, and being conformable and elastic in the longitudinal direction of the padding material.

6 Claims, 3 Drawing Figures

PERFORATED CLOSED CELL PADDING MATERIAL

BACKGROUND OF THE INVENTION

This invention relates to a perforated, closed cell foam padding material useful with orthopedic devices.

Treatment of body skeletal abnormalities such as bone fractures usually involves the immobilization of a portion of the body, which is normally provided by some form of casting material. For a long time casting material was made of plaster of paris or fabric impregnated with plaster of paris; these materials have many disadvantages, among them being unduly heavy, not sufficiently strong in many instances, and not being impervious to water and other fluids. More recently, casts have been made of materials such as Fiberglas and polyurethane for the reasons of lighter weight, greater strength, and imperviousness to liquids so as to allow the patient to immerse the affected limb in water for bathing, swimming or for physical therapy. Although these improved casting materials lived up to their original promise, very little attention has been given to the padding material under the cast, which is a prime component of the casting system. Such casts normally must remain in place on the body for a long period of time and often result in considerable discomfort and trauma to the patient. Traditionally cotton fabric, polypropylene and other materials of this nature have been used as padding material under casts to provide protection for the skin under the cast. However, such materials absorb moisture and thus accumulate moisture and cause the padding to become soggy; thus, the standard technique of using an electric hair dryer for drying the padding, through the layers of the casting material, was a long and arduous procedure. Unless the padding material is kept reasonably dry, itching, skin irritation and development of fungal infection may result, the problem being accentuated by normal perspiration. Moreover, soggy padding material does not serve its intended function of decreasing the discomfort and trauma to the patient cuased by chafing and pressure against the cast by various protuberances of the anatomy.

A variety of other materials have been tried, with minimal success, to provide a cast padding material which will not absorb moisture, that will allow for moisture vapor transmission and which will provide a resilient cushion between the cast and the body. Such materials include stockinet material of knitted or woven, non-wetting, crystalline polypropylene material (U.S. Pat. No. 3,881,473), sleeves made of non-wetting polyethylene or polypropylene yarn (U.S. Pat. No. 3,882,857), and a closed cell polymeric foam formed of polyethylene, polypropylene, polyurethane or polystyrene (U.S. Pat. No. 4,294,240).

Considering the disclosure of U.S. Pat. No. 4,294,240 in greater detail, the four specifically named foam materials are relatively non-wettable because of theclose packing of their molecular structure. Only some of them are sufficiently soft and pliable to serve as a padding between the underlying bony prominences and the rough undersurface of the cast. However, these materials do not allow for rapid transit of water molecules toward and into the perforations in the padding surface. The clinical application of the preferred perforated polyethylene foam material resulted in a high percentage of untoward skin reactions because the padding simply wouldn't dry even with extended application of heat to the outside of the cast; it retained a film of water between the skin and the padding material. The reason such perforated closed cell polyethylene foam does not perform acceptably is believed to be due to the electro-chemical attraction between the material surface and water molecules which, in terms of contact angle (i.e., the electro-chemical angle between the axis of a water molecule and the surface of the material) is quite high. Because of the high contact angle, the time required for transit of moisture entrapped under the closed areas of the foam to the perforations, where it can evaporate through the cast material, is so long as not to allow complete removal of moisture from under the padding material when heat is applied to the cast. Apart from its relatively high contact angle, the surface of polyethylene foam is relatively rough with the consequence that water molecules are trapped in the hills and valleys of the surface thereof confronting the skin. Although the surface can be made smoother by increasing the density of the closed cell foam, it is at the expense of reduced elasticity and brittleness to an extent that it no longer will acceptably conform to the surface of the encased extremity.

SUMMARY OF THE INVENTION

Applicant has discovered a padding material which is substantially non-wettable by either water from the surrounding environment such as a whirlpool bath or a swimming pool or moisture produced by the endrocrine glands of the skin, yet provides a resilient cushion and allows for water vapor transmission to effect removal of entrapped moisture into the surrounding atmosphere. The padding material, useful with modern air permeable casting materials, consists essentially of medical grade closed cell polyvinylchloride (PVC) foam, said foam being water repellent at least to the extent that water penetrates the foam with difficulty, and having extremely smooth surfaces, said padding material being conformable, resiliently compressible, containing perforations capable of passing perspiration from the human skin and other entrapped moisture therethrough, and being elastic in the longitudinal direction of the padding material.

BRIEF DESCRIPTION OF THE DRAWINGS

Applicant's padding material will be described in detail with reference to the accompanying drawings, in which.

DESCRIPTION OF THE PREFERRED EMBODIMENT

Figure 1:
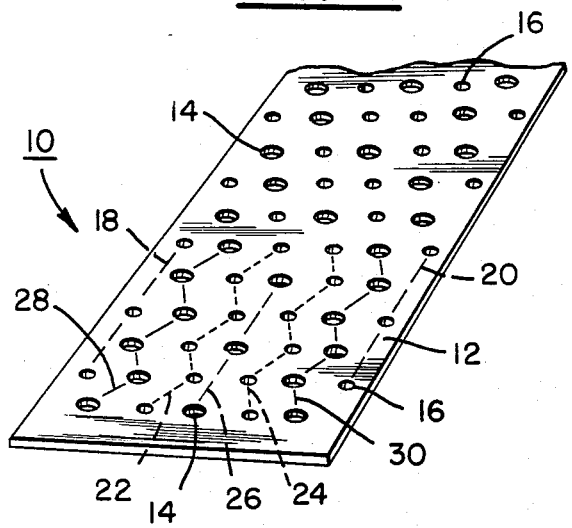
FIG. 1 is a fragmentary perspective view of a strip of the padding in a relaxed condition.

Referring to FIG. 1, the padding material 10 comprises a sheet 12 of polyvinylchloride closed cell foam which is approximately 1/16 (0.16 cm.) thick and has a density in the range from about six pounds per cubic yard to about twenty four pounds per cubic yard, a density of eighteen pounds per cubic yard having been found particularly suitable. The closed cell foam, which is of medical grade, and is produced upon a restraining sheet or liner, in a manner known to the art, when removed from the liner after the material has set, has a macroscopically smooth skin surface, i.e., one with very few hills and valleys that can interfere with the transit of moisture through the space between the foam surface and the skin of the patient. The sheet material, which may be prepared for commercial use in rolls in three or four inch widths, is perforated with a pattern of perforations of two different sizes, the larger perforations 14 preferably having a diameter of about 3/16 inch (0.48 cm.) and the smaller perforations 16 preferably have a diameter of about 1/32 inch (0.08 cm.). The padding material has a straight row of the smaller perforations spaced inwardly from each longitudinal edge by about 1/4 inch (0.64 cm.) and spaced apart approximately 1 inch (2.54 cm.) in the longitudinal direction. Two additional rows 22 and 24 of small perforations are disposed centrally between rows 18 and 20, these rows having a serpentine shape and the spacing between the perforations being roughly half that of the spacing in rows 18 and 20. The larger perforations are also arranged in three longitudinally extending rows, a straight row 26 disposed along the central axis of the strip and two serpentine-shaped rows 28 and 30 disposed slightly inwardly from the rows 18 and 20 of small perforations. The perforations in straight row 26 are spaced apart approximately 1 inch (2.54 cm.) and the perforations in the other two rows are spaced approximately 1/2 inch (1.27 cm) apart and in transverse alignment with the smaller perforations in tracks 22 and 24. The serpentine pattern of the perforations helps take up the stress of elongation of the material and prevents tearing as it is stretched and wrapped upon itself as it is applied to the body.

Figure 2:
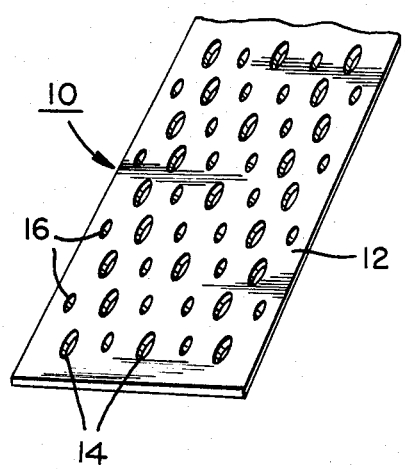
FIG. 2 is a fragmentary perspective view of a strip of the padding in a stretched condition.

As seen in FIG. 2, when the padding material is stretched in the longitudinal direction of the strip the circular perforations take on an oval shape having substantially the same area as the undistorted circular perforations. Accordingly, whether the material is in relaxed condition, is slightly stretched, or is further stretched, the perforations have significant area for removal of moisture from the skin by vapor transmission. Each perforation, whether the material is in its relaxed or stretched condition, is surrounded by an area of closed cell foam 12 considerably greater than that surrounding the slits in the padding material disclosed in U.S. Pat. No. 4,294,240. The wider spacing of the perforations, allowed by the extremely smooth surface of the closed cell PVC foam, contributes to greater strength and less risk of tearing, yet allows the padding, when applied longitudinally, to lie flat rather than roll at the edges.

Figure 3:
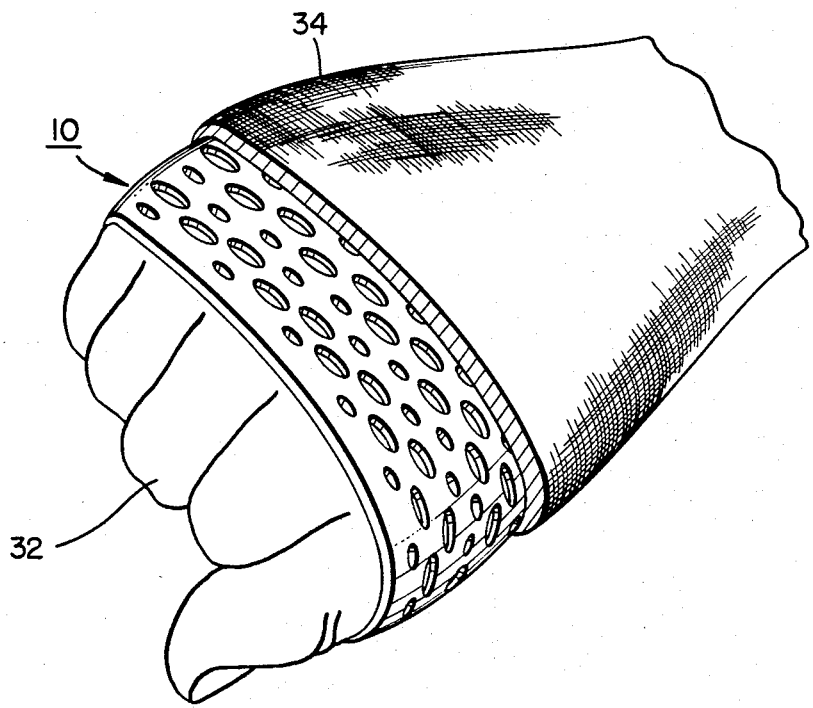
FIG. 3 illustrates the padding material in a stretched condition as applied to a fractured extremity and covered by a cast.

FIG. 3 shows the padding material 10 applied over the knuckles of a human hand 32 and shows the perforations as having a slightly oval shape, indicating that the padding was stretched in the longitudinal direction during application. Also shown in a cast 34, preferably of the air permeable type, which has been partially cut away to expose the padding material 10 covering the knuckles.

In use, a strip of padding is stretched as it is applied over the affected part of the body, normally with some overlap on itself, with the normal thickness of the padding under a cast being from one to two thicknesses of padding material. Thicker applications may be made over large protruberances. The cast material is applied over the padding material in the usual manner.

The closed cell PVC foam contains FDA approved calcium stabilizers and is therefore non-toxic, and by reason of the way it is manufactured has a macroscopically smooth surface for application next to the skin. The contact angle between this extremely smooth skin surface of the closed cell PVC foam and the axis of a water molecule is smaller than the contact angle with the skin surface of closed cell polyethylene foam, for example, and this coupled with the smooth surface makes for a very rapid transit time for water across its surface. The material is water repellant at least to the extent that water penetrates the surface of the foam with difficulty.

The closed cell PVC foam padding material having a density of eighteen pounds percubic yard conforms nicely to the shape of the body, including conforming to protuberances on the body such as elbows, knees, knuckles, etc., and is resiliently compressible. When applied to the body the padding is wrapped upon itself and is somewhat compressed by such wrapping and by having the cast material applied over it. However, the compression does not cause permanent deformation of the padding, allowing the foam to resiliently expand should the injured member atrophy due to extended inactivity and continue to fill the void between the cast and the member to maintain a tight relationship therebetween.

The padding material is essentially water repellent, but is water permeable by reason of the perforations therein which allow the vapor transmission of trapped moisture, both exogenous and inogenous, through the holes and out through the surrounding air permeable casting into the atmosphere. The improved padding material promotes the removal and dissipation of moisture in two ways: because of the smoothness of the foam surface next to the skin water actually runs down to and out the end of the cast when the encased extremity is shaken, and any entrapped moisture remaining is transported to the perforations both physically and by creating a gradient of partial pressure of water vapor by heating up the outside of the cast with a hair dryer, for example. As the areas defined by the perforations are heated, any moisture in those regions evaporates out through the air permeable casting material, causing a decrease in the partial pressure of water vapor in the perforations and drawing water vapor from under the areas of padding material surrounding the perforations to offset the decrease in partial pressure. The wider spacing of the perforations permitted by the favorable surface characteristics of the foam material gives the material greater strength and provides more padding than the slit configuration disclosed in U.S. Pat. No. 4,294,240.

Essential to the effectiveness of the described padding material is that it have the property of transporting moisture along the surface thereof that contacts the human skin, this property being a function of the electro-chemical contact angle between the foam surface and the axis of a water molecule which, in turn, depend on the density of the foam material, the electro-chemical contact angle increasing with increased density. On the other hand, if made too dense the foam material becomes less resilient and less conformable, thus placing an upper limit on the density. Accordingly, although foam densities in the range between six and twenty-four pounds per cubic yard have produced acceptable results, with a density of eighteen pounds per cubic yard giving results superior to others tested, as a general rule the foam material should be made as dense as possible while retaining practically acceptable conformability and resilience.

I claim:

1. A padding material for an immobilizing orthopedic cast, said padding material consisting essentially of closed cell polyvinyl chloride foam in strip sheet form having a density as high as possible consistent with rendering said padding material conformable, resiliently compressible and elastic in the longitudinal direction, said foam being water repellent at least to the extent that water penetrates the foam with difficuly and the sheet surface which engages the human skin being macroscopically smooth and having the property of transporting moisture therealong, said foam material having perforations capable of passing moisture such as water and perspiration from the human skin therethrough by vapor transmission.

2. The padding material of claim 1, wherein the density of said foam material is in the range between about 6 pounds and 24 pounds per cubic yard.

3. The padding material of claim 1, wherein said perforations, when said padding material is in a relaxed state, are circular perforations arranged in spaced apart rows extending along the longitudinal dimension of and generally parallel to the side edges of the strip of padding material which become oval in shape when said strip is stretched in the longitudinal direction.

4. The padding material of claim 3, wherein the perforations in the columns closest respective side edges of the strip of padding material have equal diameters smaller than the diameter of others of the perforations in the padding material and are spaced apart in the longitudinal direction about twice the longitudinal spacing of the said other perforations.

5. The padding material of claim 3, wherein said perforations have two different diameters, the area one of which is about twice the area of the other.

6. The padding material of claim 4, wherein the area of the said others of the perforations is about twice the area of the smaller perforations.

* * * * *